US008853798B2

(12) United States Patent
Merz

(10) Patent No.: US 8,853,798 B2
(45) Date of Patent: Oct. 7, 2014

(54) INTEGRATED CIRCUIT WITH SENSOR AND METHOD OF MANUFACTURING SUCH AN INTEGRATED CIRCUIT

(75) Inventor: Matthias Merz, Leuven (BE)

(73) Assignee: NXP, B.V., Eindhoven (NL)

( * ) Notice: Subject to any disclaimer, the term of this patent is extended or adjusted under 35 U.S.C. 154(b) by 12 days.

(21) Appl. No.: 13/556,676

(22) Filed: Jul. 24, 2012

(65) Prior Publication Data

US 2013/0032902 A1  Feb. 7, 2013

(30) Foreign Application Priority Data

Aug. 3, 2011 (EP) .................................. 11176484

(51) Int. Cl.
| | | |
|---|---|---|
| H01L 27/14 | (2006.01) | |
| H01L 21/00 | (2006.01) | |
| H01L 21/339 | (2006.01) | |
| G01R 27/08 | (2006.01) | |
| G01N 27/12 | (2006.01) | |
| G01N 33/18 | (2006.01) | |

(52) U.S. Cl.
CPC ............ *G01N 27/128* (2013.01); *G01N 27/125* (2013.01); *G01N 27/121* (2013.01); *G01N 33/18* (2013.01); *G01N 33/1826* (2013.01)
USPC .............. 257/414; 438/49; 438/148; 324/694

(58) Field of Classification Search
CPC .............. G01N 27/128; G01N 27/125; G01N 33/1826; G01N 33/18
USPC ............. 257/414, E27.122, E21.002; 438/22, 438/49, 148
See application file for complete search history.

(56) References Cited

U.S. PATENT DOCUMENTS

| | | | |
|---|---|---|---|
| 4,215,564 A | 8/1980 | Lawson et al. | |
| 5,756,878 A | 5/1998 | Muto et al. | |
| 6,111,280 A | * 8/2000 | Gardner et al. | ............... 257/253 |
| 7,670,046 B2 | 3/2010 | Mitov | |

(Continued)

FOREIGN PATENT DOCUMENTS

| | | |
|---|---|---|
| EP | 2 230 507 A1 | 9/2010 |
| EP | 2 336 757 A1 | 6/2011 |
| WO | 2005/095936 A1 | 10/2005 |

OTHER PUBLICATIONS

Neda, T., et al; "A Polysilicon Flow Sensor for Gas Flowmeters," Tranducers '95, Eurosensors IX; 8$^{th}$ Intl. Conf. on Solid-State Sensors and Actuators, and Eurosensors IX, 4 pgs. (1995).

(Continued)

*Primary Examiner* — Long K. Tran
*Assistant Examiner* — Dzung Tran

(57) ABSTRACT

Disclosed is an integrated circuit comprising a substrate (10) carrying a plurality of circuit elements; a metallization stack (12, 14, 16) interconnecting said circuit elements, said metallization stack comprising a patterned upper metallization layer comprising a first metal portion (20) and a second metal portion (21); a passivation stack (24, 26, 28) covering the metallization stack; a gas sensor including a sensing material portion (32, 74) on the passivation stack; a first conductive portion (38) extending through the passivation stack connecting a first region of the sensing material portion to the first metal portion; and a second conductive portion (40) extending through the passivation stack connecting a second region of the sensing material portion to the second metal portion. A method of manufacturing such an IC is also disclosed.

15 Claims, 11 Drawing Sheets

(56) References Cited

U.S. PATENT DOCUMENTS

Figure 1:
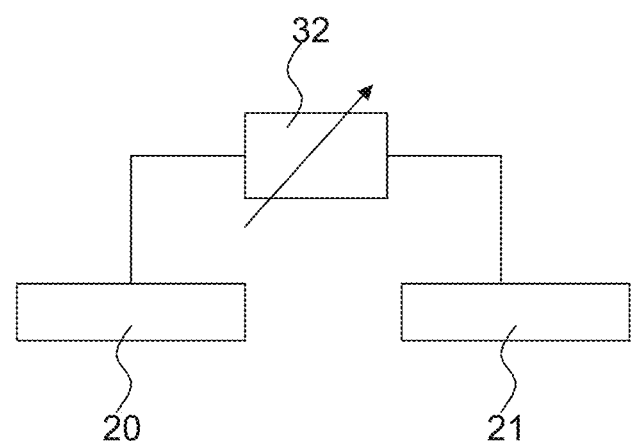

| | | | |
|---|---|---|---|
| 2002/0118027 A1* | 8/2002 | Routkevitch et al. | 324/694 |
| 2003/0010119 A1* | 1/2003 | Toyoda | 73/335.04 |
| 2004/0140501 A1* | 7/2004 | Kim | 257/328 |
| 2005/0097941 A1* | 5/2005 | Sandvik et al. | 73/31.06 |
| 2005/0218465 A1* | 10/2005 | Cummins | 257/414 |
| 2009/0158859 A1 | 6/2009 | Huang et al. | |
| 2010/0192518 A1* | 8/2010 | Cannon, Jr. | 53/434 |
| 2012/0211845 A1 | 8/2012 | Daamen et al. | |
| 2013/0032903 A1 | 2/2013 | Merz et al. | |
| 2013/0042669 A1 | 2/2013 | Humbert et al. | |

OTHER PUBLICATIONS

Wu, Y. E., et al "Fabrication and Characterization of Thermal Conductivity Detectors (TCDs) of Different Flow Channel and Heater Designs," Sensors and Actuators A 100, pp. 37-45 (2002).

"Pellistor Application Note 5, Thermal Conductivity Sensors, e2v"; A1A-Pellistor AN5, Issue 1; 2 pages (Mar. 2007).

Datasheet, "NAP-21A", Nemoto & Co., Ltd., retrieved from the Internet on Jul. 18, 2012 at http://www.nemoto.co.jp/en/products/sensor/manual/nap-21a.html, 1 pg. (2008).

Datasheet, "Orbisphere TC Sensor Selective Gas Measurement", Orbisphere 31XXX, 2 pgs. (Dec. 2009).

Datasheet, "Microsens Thermal Conductivity Sensor—MTCS-2202, Natural Gas (Methane) Sensor"; Microsens SA, 4 pgs. (undated, believed to be prior to Oct. 20, 2011).

Extended European Search Report for European patent appln. No. 11176484.1 (Dec. 14, 2011).

Extended European Search Report for European patent appln. No. 11191420.6 (May 3, 2012).

* cited by examiner

INTEGRATED CIRCUIT WITH SENSOR AND METHOD OF MANUFACTURING SUCH AN INTEGRATED CIRCUIT

CROSS-REFERENCE TO RELATED APPLICATIONS

This application claims the priority under 35 U.S.C. §119 of European patent application no. 11176484.1, filed on Aug. 3, 2011, the contents of which are incorporated by reference herein.

The present invention relates to an integrated circuit (IC) comprising a substrate carrying a plurality of circuit elements; a metallization stack interconnecting said circuit elements, said metallization stack comprising a patterned upper metallization layer comprising a first metal portion; a passivation stack covering the metallization stack; and a sensor.

The present invention further relates to a method of manufacturing such an IC.

Nowadays, integrated circuits (ICs) may comprise a plethora of sensors, such as gas sensors, relative humidity (RH) sensors, specific analyte detection sensors, and so on. Such sensors may be included in the IC design for a number of reasons.

For instance, a gas sensor may be included in an IC to detect a change in the ambient conditions of a product tagged with the chip such that product quality control can be achieved by monitoring the sensor readings of the chip. This can for instance be used to accurately predict the remaining shelf life of the product, e.g. perishable food stuff. The gas sensor may for instance be adapted to determine changes in the $CO_2$ content of the ambient atmosphere. Alternatively, the gas sensor may be used to detect changes in the gas composition of larger environment such as buildings or may be used in medical application domains, e.g. in breathing apparatuses.

It is particularly relevant to mass market applications such as RF tags for product monitoring that the gas sensor functionality can be added to the IC with limited additional cost, as there is a large price pressure on such ICs; i.e. they have to be produced cheaply in order to be commercially attractive.

It is clear that there is a desire for the integration of a variety of sensors such as gas sensor onto an IC in a cost-effective manner.

SUMMARY OF THE INVENTION

The present invention seeks to provide an IC comprising a gas sensor that can be readily provided using standard IC manufacturing methods.

The present invention further seeks to provide a method of manufacturing such an IC.

According to an aspect of the present invention, there is provided an integrated circuit comprising a substrate carrying a plurality of circuit elements; a metallization stack interconnecting said circuit elements, said metallization stack comprising a patterned upper metallization layer comprising a first metal portion and a second metal portion; a passivation stack covering the metallization stack; a gas sensor including a sensing material portion on the passivation stack; a first conductive portion extending through the passivation stack connecting a first region of the sensing material to the first metal portion; and a second conductive portion extending through the passivation stack connecting a second region of the sensing material to the second metal portion.

The present invention is based on the insight that gas-sensitive materials may be deposited on top of the passivation stack and connected to contacts in the metallization stack using standard processing techniques. In an embodiment, the sensing material comprises a porous layer comprising at least one metal oxide. Such a porous layer may for instance be a porous substrate layer is functionalized with said at least one metal oxide, which can be formed using standard processing steps; the pores may be formed by standard etching techniques and the metal oxide can be formed using standard deposition techniques such as ALD, CVD, PE-CVD and so on. Alternatively, the porous substrate layer comprises anodic aluminium oxide, which may be formed by an aluminum deposition followed by an anodic oxidation step, thus forming a self-aligned nanoporous material as is known per se.

The sensing material portion may comprise a T-shape such that a recess is located between the sensing material portion and the passivation stack. This is particularly advantageous if the sensing material portion is formed by the oxidation of a metal portion, where incomplete oxidation may cause a metal track, e.g. at the surface of the sensing portion facing the passivation stack to extend between the first and second conductive portions, thus shorting the sensing material. The recess prevents such a residual metal track from reaching the conductive portions, thus preventing the short circuit of the sensing material.

Alternatively, such a short circuit may be prevented by separating the sidewalls of the sensing material portion from the first and second conductive portions by respective electrically insulating sidewall spacers.

In a further alternative embodiment, the first and second conductive portions comprise respective bond wires, which do not contact the sidewalls of the sensing portion, thus also preventing the aforementioned short circuit.

The integrated circuit may further comprise a heating element in an metallization layer of the metallization stack, said heating element being located opposite the sensing material portion. This has the advantage that the operating temperature of the gas sensor may be controlled, thus facilitating the detection of gases that can only be detected at elevated temperatures and the acceleration of the reaction and recovery time of the gas sensor. The metallization layer housing the heating element preferably is the upper metallization layer.

According to another aspect of the present invention, there is provided a method of manufacturing an integrated circuit, comprising providing a substrate carrying a plurality of circuit elements; forming a metallization stack interconnecting said circuit elements, said metallization stack comprising a patterned upper metallization layer comprising a first metal portion and a second metal portion; forming a passivation stack covering the metallization stack; forming a gas sensor including a sensing material portion on the passivation stack; opening the passivation stack to expose the first metal portion and the second metal portion; and forming a first conductive portion between a first region of the sensing material portion and the first metal contact and second conductive portion between a second region of the sensing material portion and the second metal contact.

Such a method facilitates the formation of a gas sensor in a standard manufacturing process, in particular a standard CMOS process.

The method may further comprise selectively removing edge portions of the sensing material portion to form a recess between the sensing material portion and the passivation stack prior to forming the first conductive portion and the second conductive portion to prevent the formation of a short circuit between the conductive portions as previously explained.

In an alternative embodiment, the method further comprises forming electrically insulating sidewall spacers adjacent to the sensing material portion prior to forming the first conductive portion and the second conductive portion to prevent the formation of a short circuit between the conductive portions as previously explained.

In yet another alternative embodiment, the step of forming a first conductive portion between a first region of the sensing material portion and the first metal contact and second conductive portion between a second region of the sensing material portion and the second metal contact comprises forming a first bond wire between the first region of the sensing material portion and the first metal contact and a second bond wire between the second region of the sensing material portion and the second metal contact to prevent the formation of a short circuit between the conductive portions as previously explained.

The step of forming a gas sensor including a sensing material portion on the passivation stack may comprise forming a substrate portion on the passivation stack; etching pores into said substrate portion; and at least partially filling said pores with at least one metal oxide. This has the advantage that the risk of the occurrence of a short circuit due to the incomplete oxidation of a metal portion can be largely avoided.

Alternatively, the step of forming a gas sensor including a sensing material portion on the passivation stack comprises forming an aluminum layer portion on the passivation stack; and anodically oxidizing said aluminum layer portion. This has the advantage that the sensing material portion may be formed in a simple two-step process, thus yielding a particularly cost-effective IC.

BRIEF DESCRIPTION OF THE EMBODIMENTS

Figure 2:
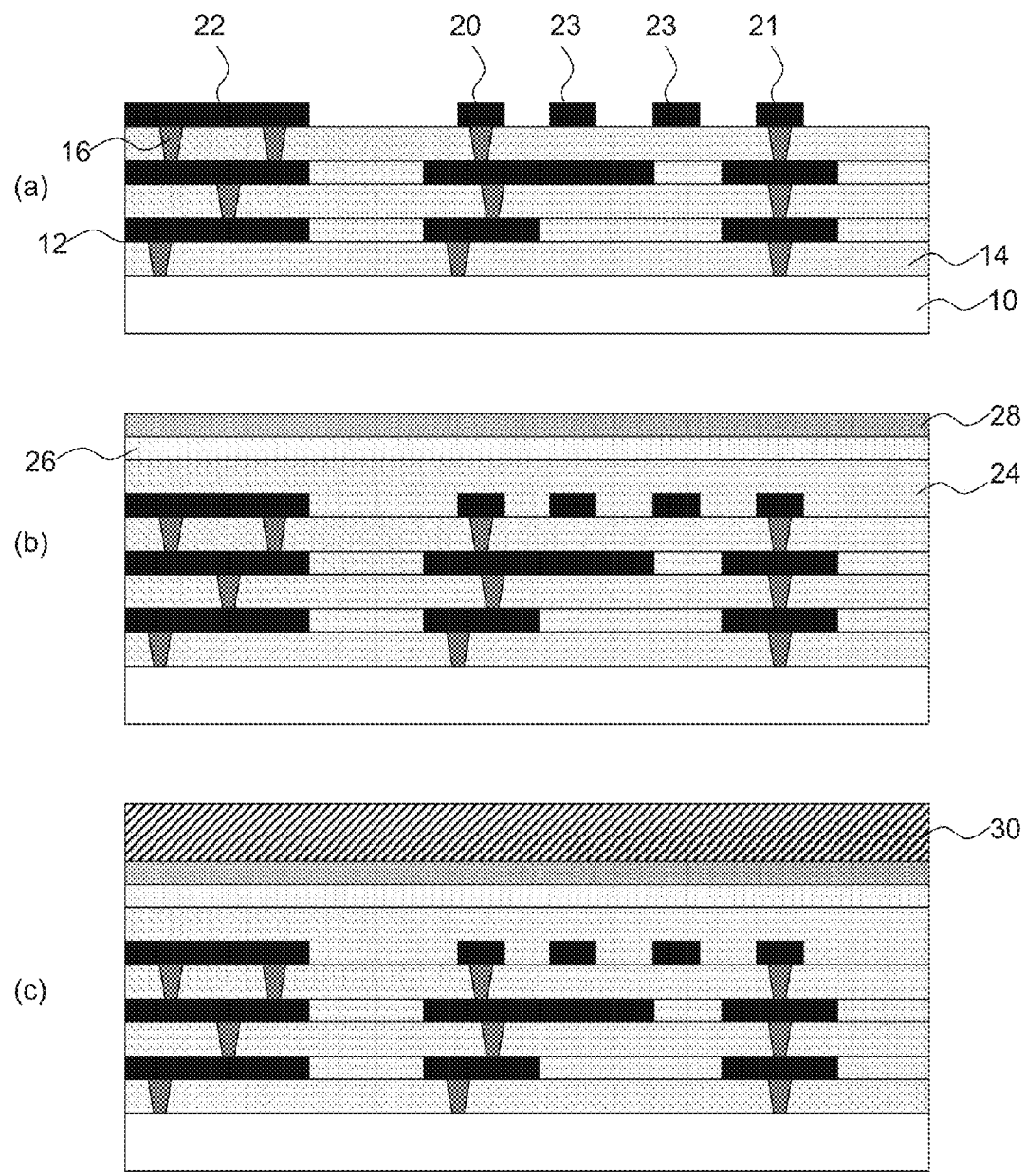
Figure 2:
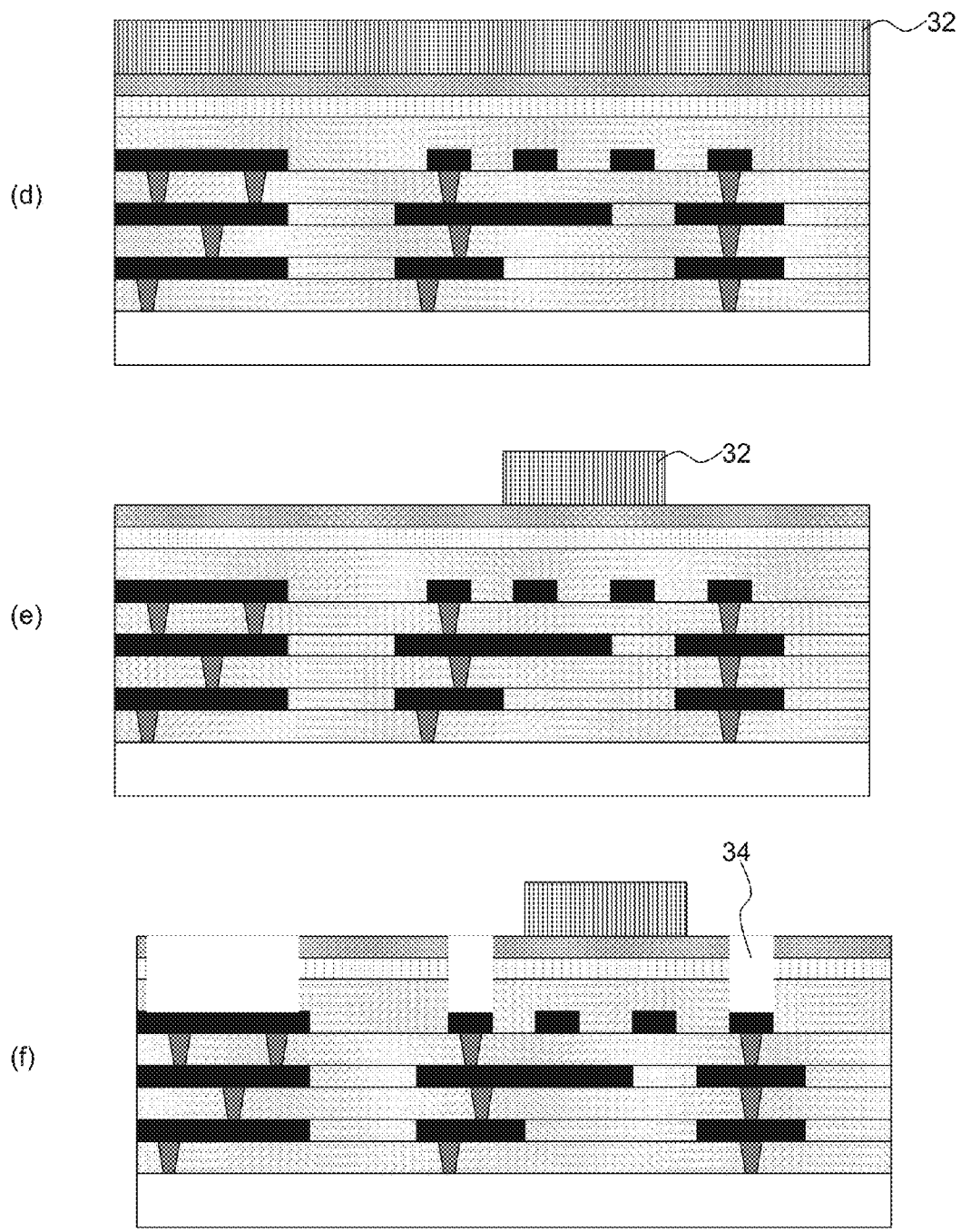
Figure 2:
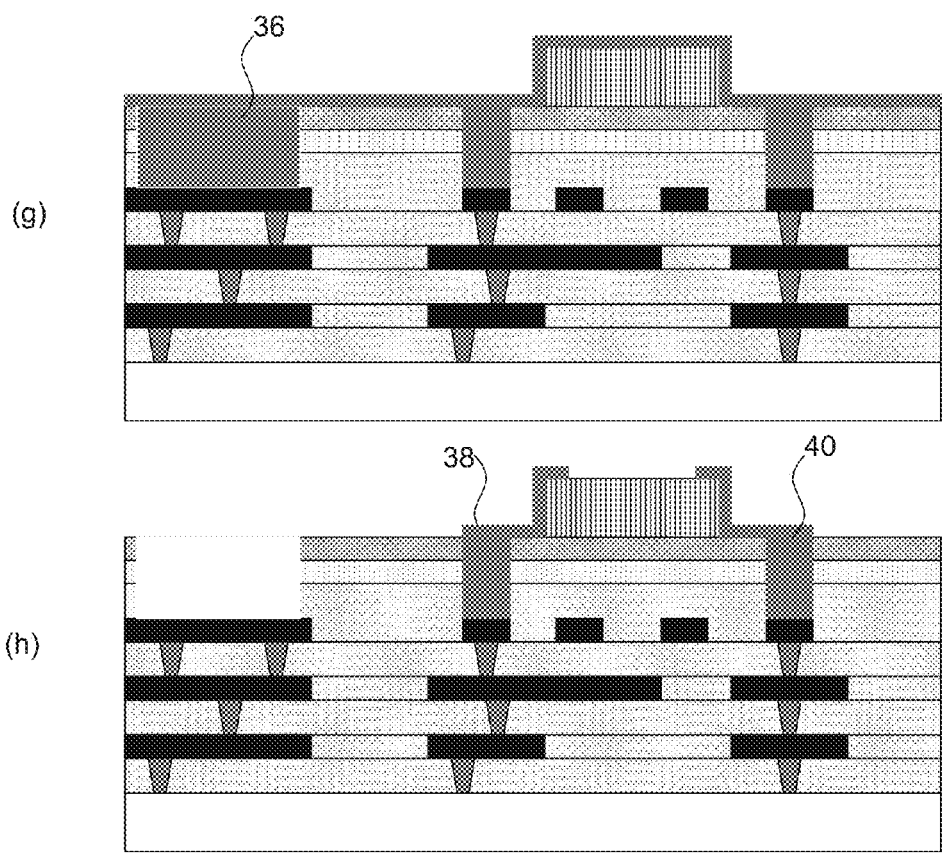
Figure 3:
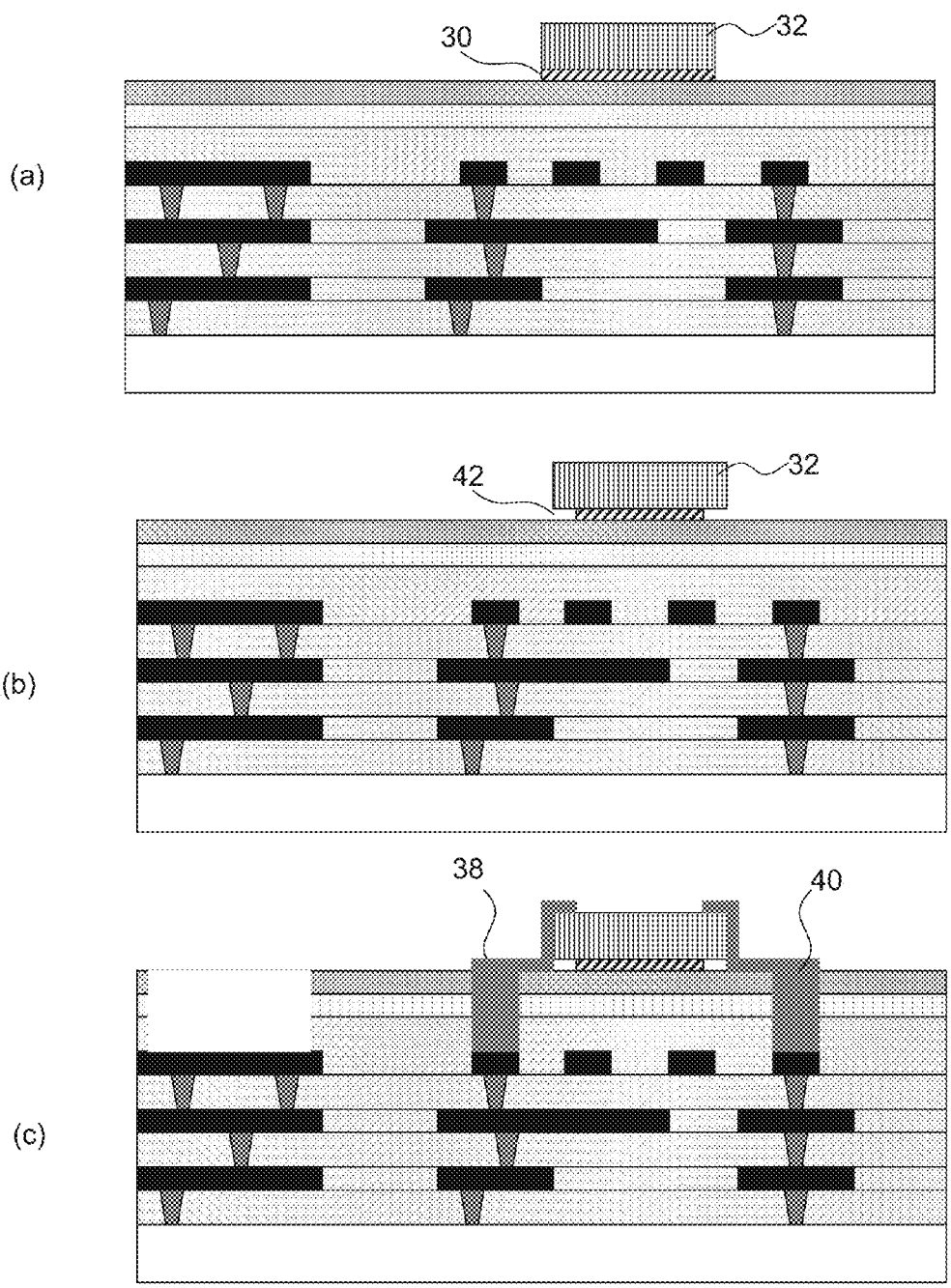
Figure 4:
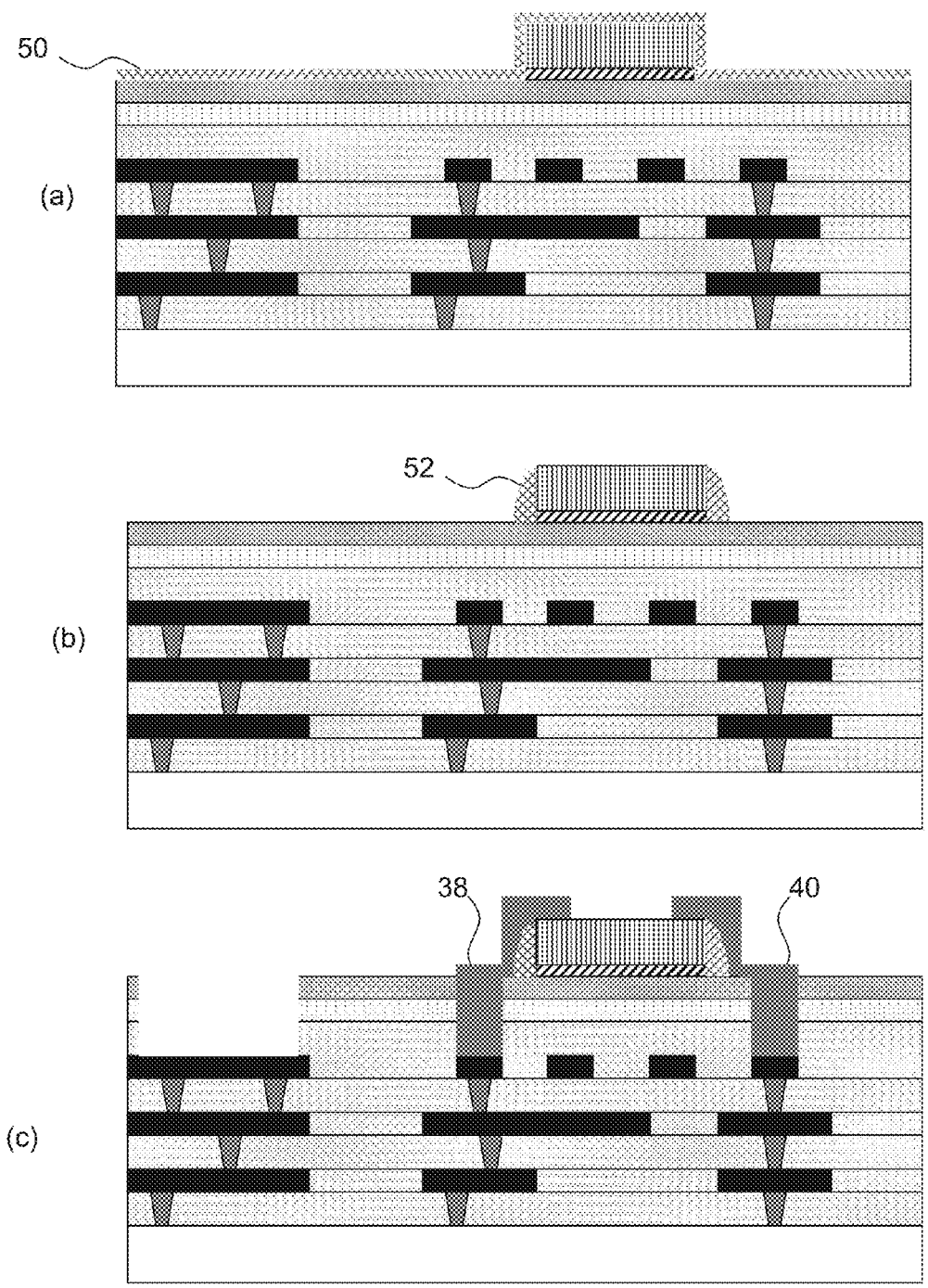
Figure 5:
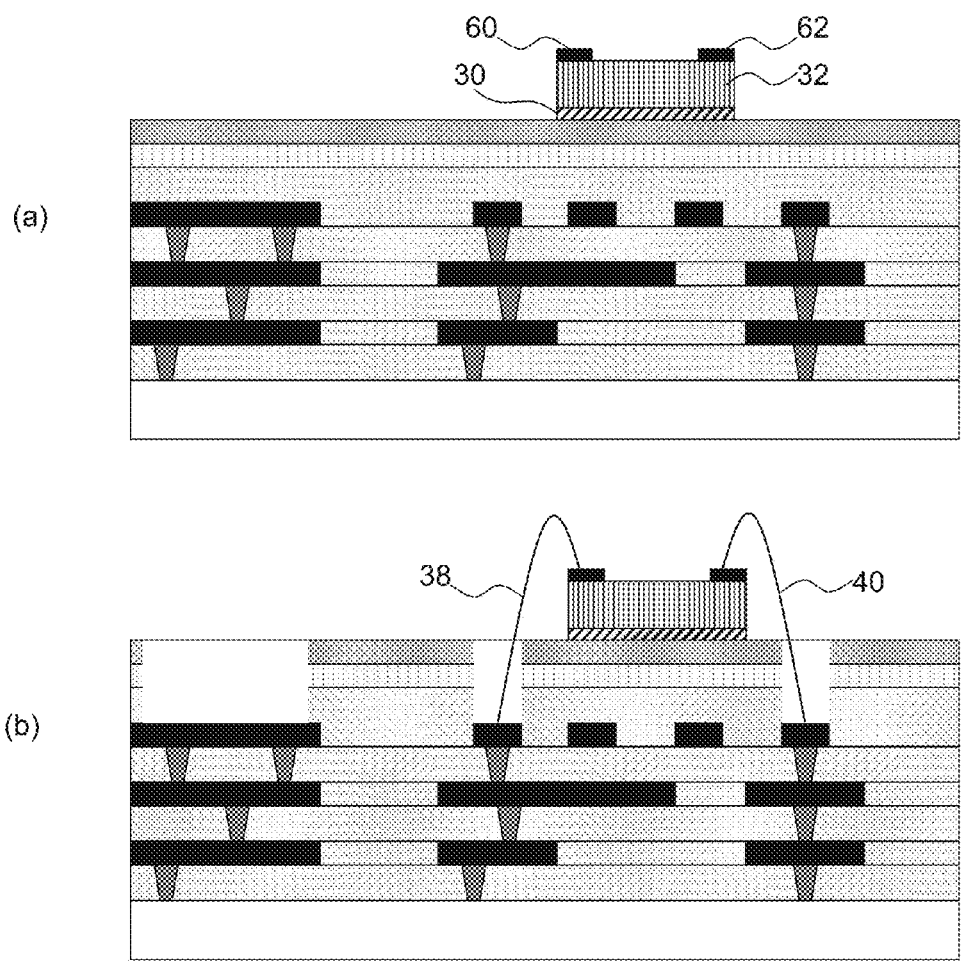
Figure 6:
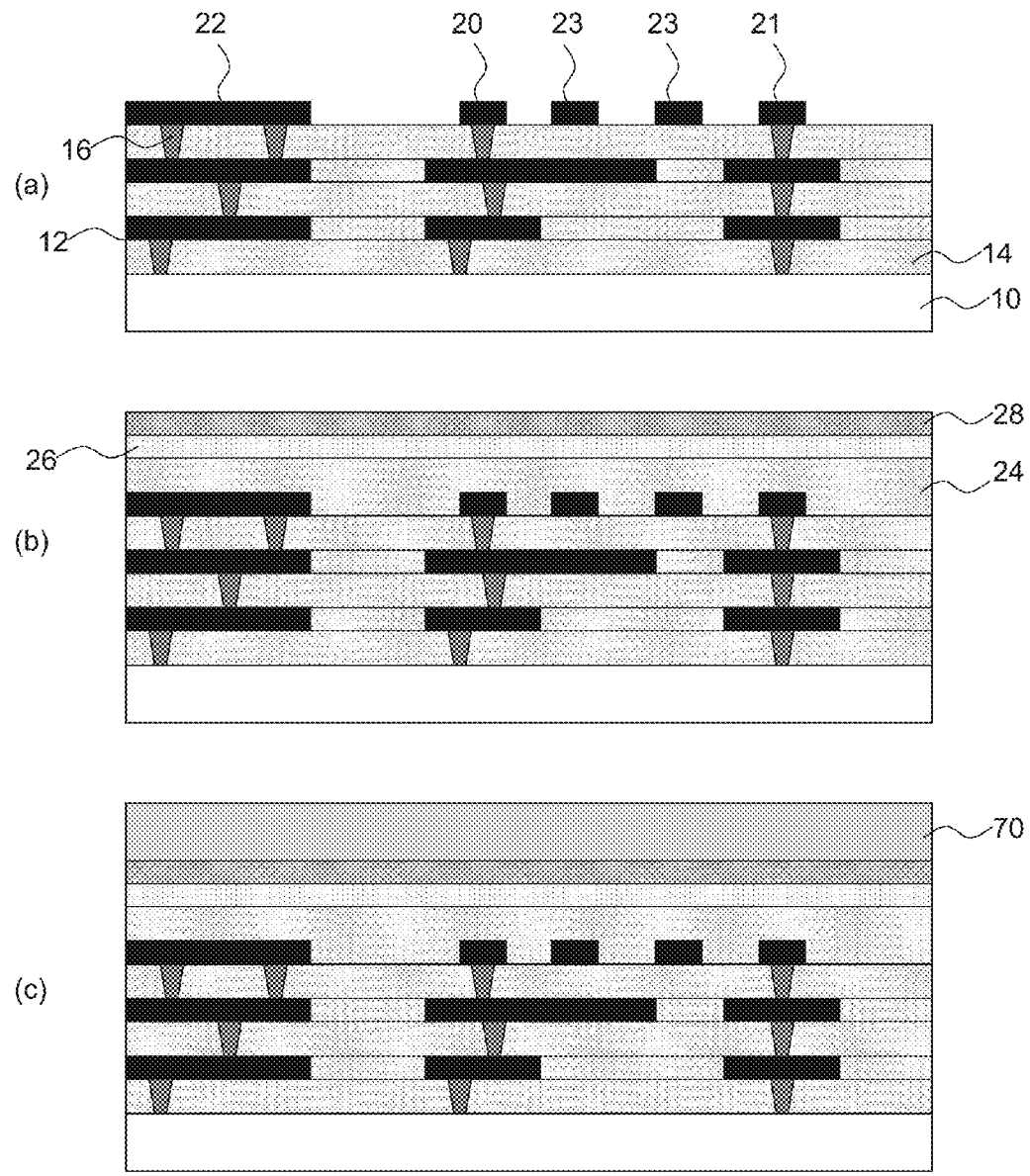
Figure 6:
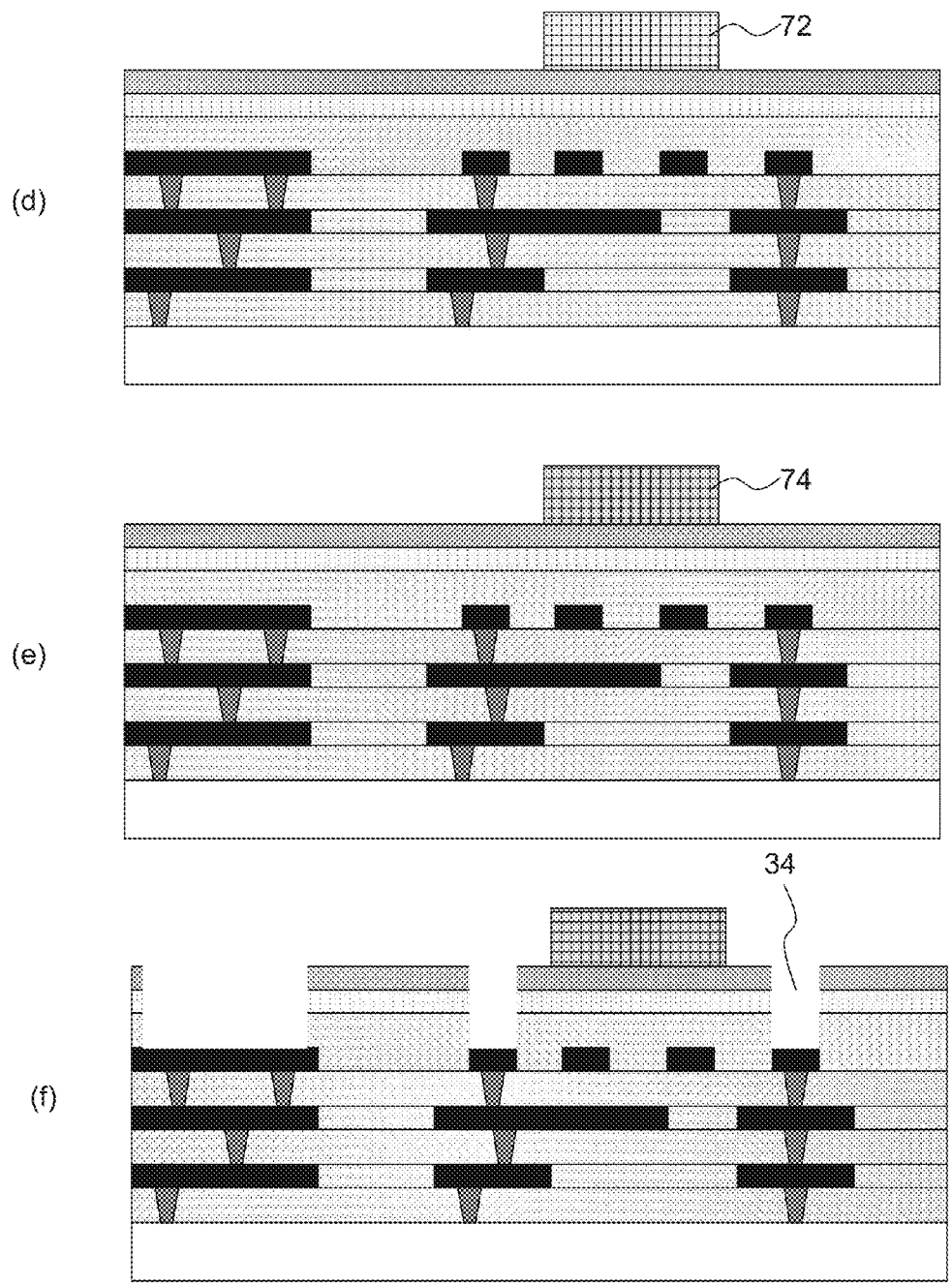
Figure 6:
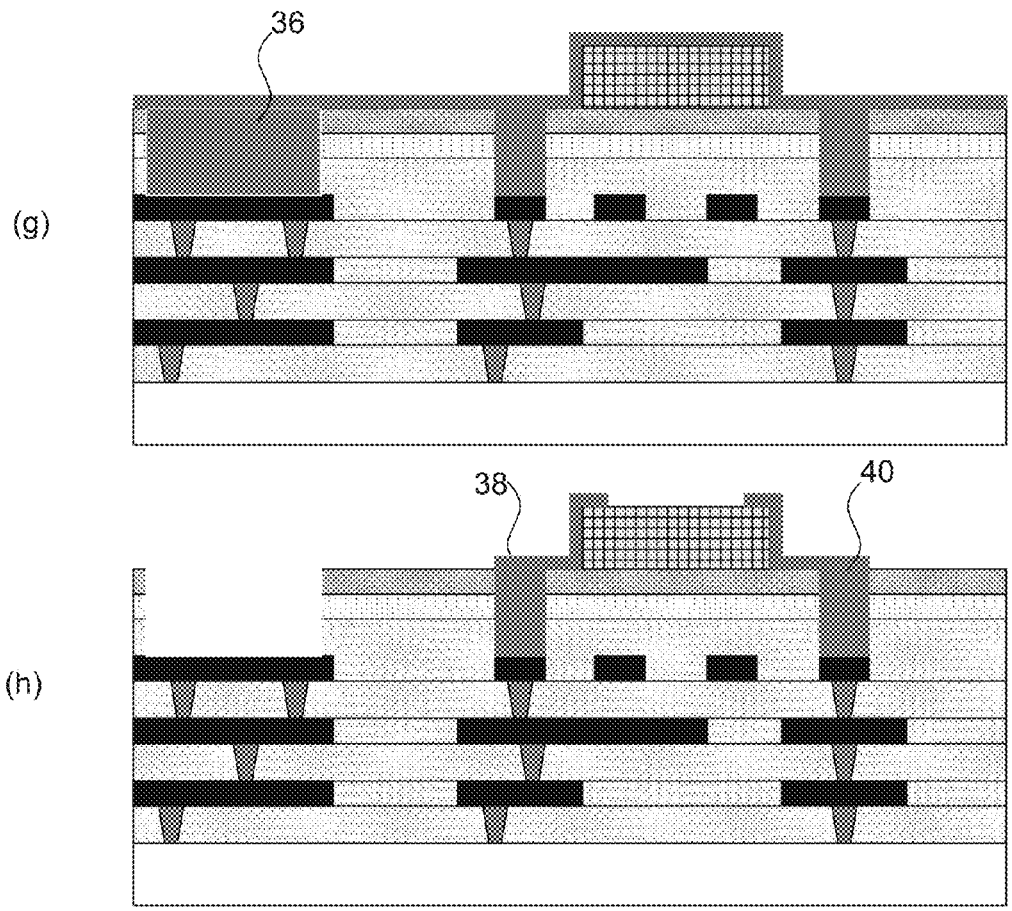
Figure 7:
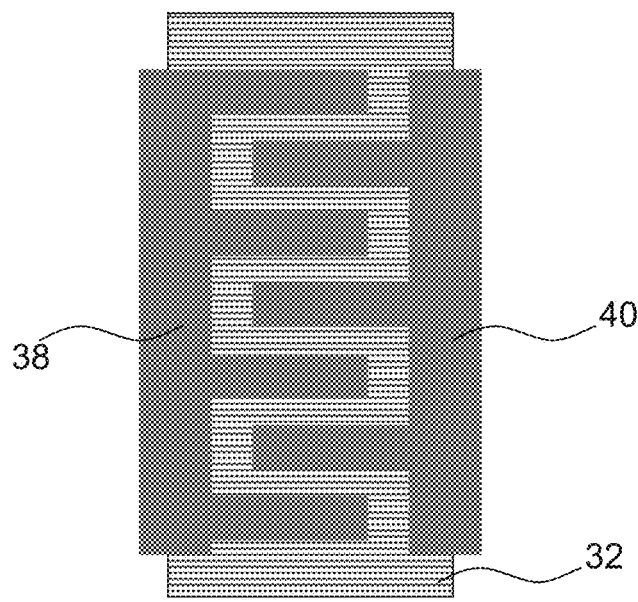
Figure 8:
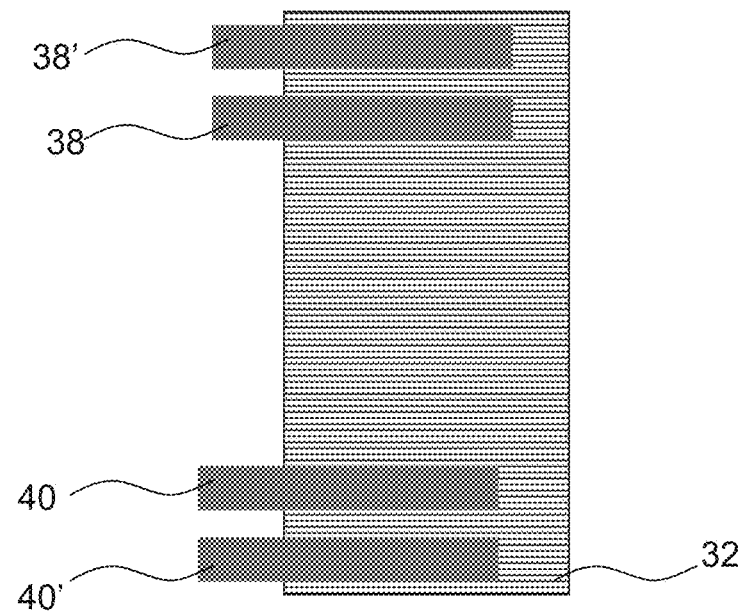

Embodiments of the invention are described in more detail and by way of non-limiting examples with reference to the accompanying drawings, wherein:

FIG. 1 schematically depicts an example operating principle of a gas sensor;

FIG. 2 schematically depicts a method to manufacture an IC with a gas sensor in accordance with an embodiment of the present invention;

FIG. 3 schematically depicts a method to manufacture an IC with a gas sensor in accordance with another embodiment of the present invention;

FIG. 4 schematically depicts a method to manufacture an IC with a sensor in accordance with yet another embodiment of the present invention;

FIG. 5 schematically depicts a method to manufacture an IC with a sensor in accordance with yet another embodiment of the present invention;

FIG. 6 schematically depicts a method to manufacture an IC with a sensor in accordance with yet another embodiment of the present invention;

FIG. 7 schematically depicts a top view of an IC comprising a gas sensor according to yet another embodiment of the present invention; and FIG. 8 schematically depicts a top view of an IC comprising a gas sensor according to yet another embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 schematically depicts an operating principle of a gas sensor. A gas-sensitive material portion 32 is placed in a conductive path between a first contact 20 and a second contact 21. The gas-sensitive material portion 32 acts as a variable resistor with its resistance dependent on the level of exposure of the gas to be monitored. The adsorption of gas to the surface of the gas-sensitive material portion 32 changes the electrical resistance of the material, either by the occurrence of an oxidation reaction in which electrons are transferred from the gas-sensitive material portion 32 to the gas or a reduction reaction in which electrons are transferred from the gas to the gas-sensitive material portion 32. As the reaction rate scales with the concentration of the gas, the measured resistance can be translated into a gas concentration. The gas-sensitive material portion 32 is typically chosen to have a high specific surface area such that relatively large volumes of gas can adsorb to the gas-sensitive material portion 32, thus improving signal-to-noise characteristics of the gas sensor.

FIG. 2 schematically depicts the various steps of a method of manufacturing an IC with a gas sensor, i.e. a sensor exposed to the environment of the IC in accordance with an embodiment of the present invention, in which the gas sensor can be integrated using processing steps that are readily available in the manufacturing process of the IC. The manufacturing process preferably is a CMOS process.

As shown in step (a), an IC may be provided comprising a substrate 10 onto which a metallization stack is formed. Such a metallization stack typically comprises a stack of patterned metal layers 12 electrically insulated from each other by electrically insulating, i.e. dielectric layers 14. Metal portions in different metallization layers 12 may be conductively coupled to each other by means of vias 16 extending through dielectric layers 14 separating such metal portions from each other. The substrate 10 may be any suitable substrate material, e.g. single crystal Si, SiGe, silicon on insulator and so on, and may carry a plurality of circuit elements such as transistors, diodes and so on.

Equally, the metallization stack may be formed in any suitable manner, and may contain any suitable number of metal layers 12 and dielectric layers 14. It should be understood that three metal layers are shown by way of non-limiting example only.

Each metal layer 12 and each dielectric layer 14 is depicted as a single layer in FIG. 2 for the sake of clarity only. It should be appreciated that such layers may consist of a number of stacked sub-layers, for instance in a submicron CMOS process, stacks of Ti, TiN, AlCu, TiN may be used to define a single metal layer in the metallization stack.

Each of the dielectric layers 14 may also comprise more than a single layer. For instance, such a dielectric layer may be a stack comprising FSG (fluorosilicate glass), $SiO_2$ and HDP oxide (High Density Plasma) any other suitable dielectric material combination. Other suitable materials may also be used.

Similarly, it will be apparent that the vias 16 may be formed from more than a single material. For instance, in a 140 nm CMOS technology, a via 16 may be formed by a TiN liner and a W plug. Other semiconductor processes may use different materials, e.g. Cu for the metal layers 12 and vias 16.

In FIG. 2, the upper metal layer of the metallization stack comprises a first electrode portion 20, a second electrode portion 21, a bond pad portion 22 and an optional heating element 23. The heating element 23 may be implemented as a meander line in the upper metal layer. Alternatively, the heating element 23 may be omitted.

In step (b), the metallization stack is covered by a passivation stack, which may comprise the deposition of a high density plasma oxide 24 followed by an oxide planarization step, e.g. a chemical mechanical polishing (CMP) step, after which a $SiO_2$ layer 26 and a $Si_3N_4$ layer 28 may be deposited to any suitable thickness. Other layer materials may also be contemplated for the passivation stack. It is known per se to the skilled person how to form such a passivation stack such that this will not be elaborated upon for reasons of brevity only.

The method proceeds as shown in step (c), in which an aluminum layer 30 is deposited onto the passivation stack. This deposition may for instance be achieved using chemical vapor deposition (CVD) or plasma vapor deposition (PVD). Preferably, the aluminum layer 30 has a thickness of one to several micrometers, e.g. 5 μm or more.

In step (d), the aluminum layer 30 is anodically oxidized to convert the aluminum layer 30 into an anodic aluminum oxide 32. This may for instance be achieved by immersing the wafer in a liquid electrolyte/acid bath and applying a voltage across the aluminum layer 30 and an electrode in the immersion bath. It is noted that the other components of the IC remain protected by the passivation stack.

Anodically oxidized aluminum is a self-organized nanoporous material that contains a high density of cylindrical nanopores that align perpendicularly to the surface supporting the nanopores. This support may for instance be an unreacted portion of the aluminum layer 30, which may be located at the bottom of the oxidized portion as well as in between its pores. Typically, a dense aluminum oxide film is formed separating the pores from the aluminum support. By controlling the anodizing reaction conditions, the pore diameter may be tuned in a large range, i.e. from 5 to several hundreds of nanometers, with the corresponding pore density ranges from $10^{12}$-$10^9$ $cm^{-1}$. The pores increase the specific surface area of the material, thus providing a larger surface area for the gas to adhere to.

Next, the anodic aluminum oxide 32 may be functionalized to make the anodic aluminum oxide 32 sensitive to a particular type of gas, e.g. $CO_2$. This may for instance be achieved by deposition a metal oxide such as ZnO onto the anodic aluminum oxide 32, which preferably is performed in a highly conformal manner to ensure efficient penetration of the metal oxide into the pores of the anodic aluminum oxide 32. This may for instance be achieved by atomic layer deposition (ALD).

As shown in step (e), the anodic aluminum oxide 32 is patterned into a sensing material portion on the passivation stack located above (i.e. opposite to) the heating element 23 in the upper metal layer, if present. This patterning may be achieved using patterning techniques that are well-known per se; for instance, a resist may be deposited, exposed through a lithographic mask and developed to cover only the part of the anodic aluminum oxide layer 32 to remain on the passivation stack, after which the exposed anodic aluminum oxide 32 is etched away stopping on the passivation stack, followed by the subsequent removal of the resist from the remaining portion of the anodic aluminum oxide 32.

Next, the passivation stack is opened by forming trenches 34 that at least expose the contacts 20, 21 and may also expose the bond pad 22. This is shown in step (f). This patterning may be achieved using patterning techniques that are well-known per se; for instance, a resist may be deposited, exposed through a lithographic mask and developed to expose only the parts of the passivation stack to be opened, after which the exposed passivation stack is etched away stopping on the upper metal layer of the metallization stack, followed by the subsequent removal of the resist from the remaining portions of the passivation stack.

The method then proceeds as shown in step (g), in which a metal layer 36 defining the sensor contacts is deposited in any suitable manner, e.g. by PVD or CVD, after which the metal layer 36 is patterned as shown in step (h) to define the first conductive portion 38 that connects one side of the anodized aluminum oxide portion 32 to the first electrode contact 20 and a second conductive portion 40 that connects an opposite side of the anodized aluminum oxide portion 32 to the second electrode contact 21 such that the anodized aluminum oxide portion 32 laterally extends between the first conductive portion 38 and the second conductive portion 40. As before, the patterning of the metal layer 36 may be achieved in any suitable manner, e.g. by resist deposition, lithographic exposure and development, subsequent metal layer etch and resist removal. Although in step (h) the metal 36 has been removed from the bond pad 22 it should be understood that it is equally feasible to maintain a metal portion over the bond pad 22. The IC may subsequently be finalized, e.g. packaged, in any suitable manner.

FIG. 3 depicts an alternative embodiment of the method of FIG. 2, which proceeds from the intermediate IC structure obtained after step (e) of FIG. 2. As previously explained, the anodized aluminum oxide portion 32 may still comprise an aluminum support layer, which for instance can occur when the aluminum layer 30 is not fully oxidized. This is shown in FIG. 3(a). Upon forming the first conductive portion 38 and the second conductive portion 40 as shown in FIG. 2(h), the aluminum support layer 30 may form a low-resistance conductive path between the first conductive portion 38 and the second conductive portion 40, which bypasses (short-circuits) the functionalized anodized aluminum oxide portion 32, thus disabling the gas sensor, i.e. rendering the gas sensor non-functional.

In order to prevent the occurrence of such a short-circuit an additional processing step may be added to the method of FIG. 2. This additional processing step takes place before the passivation stack is opened and is shown in FIG. 3(b). A selective aluminum etch that does not attack $Al_2O_3$ is performed, which creates an underetch or recess 42 underneath the anodic aluminum oxide portion 32 such that upon the formation of the first conductive portion 38 and the second conductive portion 40 as explained in more detail with the aid of FIG. 2 a finalized gas sensor is obtained as shown in FIG. 3(c), in which the first conductive portion 38 and the second conductive portion 40 are electrically insulated from the aluminum support layer 30 by the recess or void 42.

An alternative embodiment of electrically insulating the first conductive portion 38 and the second conductive portion 40 from the aluminum support layer 30 is shown in FIG. 4, which takes the intermediate IC structure as shown in FIG. 2(e) as starting point. A layer 50 of an electrically insulating material such as an oxide, nitride, low-k dielectric and so on, is deposited over the resulting structure as shown in step (a), followed by the patterning of the electrically insulating material into electrically insulating side wall spacers 52 as shown in step (b). This may for instance be achieved by a spacer etch, which is well-known per se.

The gas sensor may be completed as shown in FIG. 2, i.e. by opening the passivation layer and forming the first conductive portion 38 and the second conductive portion 40, which are electrically insulated from the aluminum support layer 30 by the sidewall spacers 52. The resultant structure is shown in FIG. 4(c). It is pointed out that the sidewall spacers 52 may have any suitable shape, and may for instance have a portion that extends over the upper surface of the anodic aluminum oxide portion 32 to further improve the electrical insulation of the first conductive portion 38 and the second conductive portion 40 from the aluminum support layer 30.

It is noted that FIG. 3 and FIG. 4 have in common that electrical insulation means are formed between the aluminum support layer 30 and the first conductive portion 38 and the second conductive portion 40 respectively. However, in an alternative embodiment shown in FIG. 5, contact portions 60 and 62 are formed on opposite edge portions of the upper surface of the anodic aluminum oxide portion 32, which may be achieved by a metal deposition step, e.g. a CVD or PVD deposition step, followed by the formation of a patterned resist and metal etch from the areas exposed by the patterned resist and subsequent resist removal. The passivation stack may be opened as shown in FIG. 2(f), followed by the formation of the first conductive portion 38 and the second conductive portion 40 in the form of bond wires from the first contact portion 60 to the first metal portion 20 and from the second contact portion 62 to the second metal portion 21 respectively. As the bond wires are not in physical contact with the side walls of the aluminum support layer 30 and the anodic aluminum oxide portion 32, a short-circuit of the gas sensor is avoided.

The porous material used for the gas sensor of the present invention is not limited to anodic aluminum oxide. Any suitable porous material may be used, although it is preferable for cost reasons to use materials that are already used in the IC manufacturing process.

An embodiment of the present invention using such an alternative embodiment is shown in FIG. 6. Step (a) and step (b) are completely analogous with step (a) and (b) as shown in FIG. 2 and will therefore not be described again for the sake of brevity.

In step (c), a substrate material 70, e.g. silicon, silicon oxide or silicon nitride, is deposited over the passivation stack of the IC. This may for instance be achieved using CVD or PVD deposition techniques. Alternatively, the substrate material 70 may be epitaxially grown on the passivation stack. The substrate material 70 is subsequently patterned into a substrate portion 72, which is located over the heating element 23 if present. This is shown in step (d).

The substrate 70 is typically patterned such that upon the removal of the substrate 70 from the areas other than the area of the substrate portion 72, the substrate portion 72 is made porous by etching micro-pores into the substrate portion 72. This can for instance readily be achieved by defining a mask portion over the substrate portion 72 to have openings of nanometer dimensions. It is noted that this is routinely feasible in submicron manufacturing processes such as a submicron CMOS process in which feature sizes of only a few hundred nanometers can be routinely achieved, e.g. when etching via trenches through dielectric layers.

Upon providing the porous substrate portion 72, this porous portion may be functionalized, e.g. by a high-conformal deposition of a metal oxide such as ZnO for a $CO_2$ sensor as previously explained. Other suitable functionalization materials will be apparent to the skilled person. The resulting functionalized porous substrate portion 74 is shown in step (e). The method may now proceed analogously to what has already been explained in detail in the detailed description of FIG. 2, i.e. by forming the trenches 34 through the passivation stack as shown in step (f), depositing a metal layer 36 over the resultant structure as shown in step (g) and patterning the metal layer 36 to form the first conductive portion 38 and the second conductive portion 40 connecting the gas-sensitive substrate portion 74 to the first contact portion 20 and the second contact portion 21 respectively.

It is pointed out that variations to the shown manufacturing processes will be apparent to the skilled person, such that these variations are intended to fall under the scope of the present invention.

For instance, as shown in FIG. 2-5, the aluminum layer 30 is oxidized prior to patterning. It is equally feasible to first pattern the aluminum layer 30 into the sensor portion and subsequently oxidize and functionalize this portion.

Equally, although the embodiments of FIG. 3-5 are shown as separate embodiments of the present invention, these embodiments may be combined without departing from the teachings of the present invention. For instance, bond wires 60 and 62 may be used in combination with side wall spacers 52 or the recess 42 to further reduce the risk of the aforementioned short-circuit occurring.

Similarly, in FIG. 6, the substrate layer 70 has been patterned prior to its functionalization. It is of course equally feasible to first make the substrate layer 70 porous, subsequently functionalize the porous layer after which the functionalized porous layer may be patterned into functionalized porous substrate portion 74. Alternatively, the substrate layer may first be made porous, subsequently patterned and functionalized following patterning.

Finally, it should be understood that many variants may be possible to the arrangement of the conductive portions 38 and 40 on the gas sensitive portion on the passivation stack. For instance, an arrangement with interdigitated contact portions 38 and 40 on top of the gas sensitive portion may be contemplated such that the interdigitated contact portions 38 and 40 are electrically insulated from each other by a meandering portion of the gas sensitive portion 32 or 74. An example embodiment with a gas sensitive portion 32 is shown in FIG. 7. Other arrangements that are known per se will be readily available to the skilled person.

It should furthermore be understood that the gas sensitive portion may be contacted by more than two electrodes. For instance, as shown in FIG. 8, in addition to the contact portions 38 and 40 forming an inner electrode pair, the IC may further comprise an additional pair of contact portions 38' and 40' forming an outer electrode pair. The outer electrode pair may be used to force a current through the gas sensitive portion such as a gas sensitive portion 32 as shown in FIG. 8, with the inner electrode pair being arranged to measure the voltage drop across the gas sensitive portion. Again, such an electrode arrangement is known per se and alternative arrangements will be readily available to the skilled person.

The IC of the present invention may be integrated in any suitable electronic device, e.g. a mobile communication device such as a mobile phone, personal digital assistant and so on, or may be used as a tag for an article for monitoring purposes, in which case the IC may be extended with RF functionality, e.g. an RF transceiver communicatively coupled to the sensor(s) of the IC.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:
1. An integrated circuit comprising:
   a substrate carrying a plurality of circuit elements;
   a metallization stack interconnecting said circuit elements, said metallization stack comprising a patterned upper metallization layer comprising a first metal portion and a second metal portion;
   a passivation stack covering the metallization stack;
   a gas sensor including a sensing material portion on the passivation stack;
   a first conductive portion extending through the passivation stack connecting a first region of the sensing material portion to the first metal portion; and
   a second conductive portion extending through the passivation stack connecting a second region of the sensing material portion to the second metal portion.
2. The integrated circuit of claim 1, wherein the sensing material comprises a porous layer comprising at least one metal oxide.
3. The integrated circuit of claim 2, wherein the porous layer is a substrate layer functionalized with said at least one metal oxide.
4. The integrated circuit of claim 3, wherein the at least one metal oxide is one of ZnO and $Al_2O_3$.
5. The integrated circuit of claim 2, wherein the porous layer comprises anodic aluminum oxide.
6. The integrated circuit of claim 1, wherein the sensing material portion comprises a T-shape such that a recess is located between the sensing material portion and the passivation stack.
7. The integrated circuit of claim 1, wherein sidewalls of the sensing material portion are separated from the first and second conductive portions by respective electrically insulating sidewall spacers.
8. The integrated circuit of claim 1, wherein the first and second conductive portions comprise respective bond wires.
9. The integrated circuit of claim 1, further comprising:
   a heating element in a metallization layer of the metallization stack, said heating element being located opposite the sensing material portion.
10. The integrated circuit of claim 1, wherein the sensing material is patterned with lithographic and deposition techniques so that only the portion of the sensing material deposited remains on the passivation stack.
11. The integrated circuit of claim 1, wherein the sensing material includes a track extending between the first and second conductive portions which shorts the sensing material.
12. The integrated circuit of claim 11, wherein the track is a metal track formed by incomplete processing of the sensing material.
13. The integrated circuit of claim 1, further comprising:
   a recess between the sensing material portion and the passivation stack, whereby the recess prevents a short-circuit of the sensing material portion.
14. The integrated circuit of claim 1, further comprising:
   an insulating sidewall spacer between sidewalls of the sensing material portion and at least one of the conductive portions, whereby the spacer prevents a short-circuit of the sensing material portion.
15. The integrated circuit of claim 1, wherein at least one of the conductive portions is a bond-wire which does not contact sidewalls of the sensing material portion, whereby the bond-wire prevents a short-circuit between the conductive portions.

\* \* \* \* \*